United States Patent [19]

Johnson et al.

[11] 4,342,868

[45] Aug. 3, 1982

[54] 2-DESCARBOXY-2-(TETRAZOL-5-YL)-16,16-DIMETHYL-17-(2-FURYL)-ω-TRISNOR-PROSTAGLANDIN $E_2$

[75] Inventors: Michael R. Johnson, Gales Ferry; Thomas K. Schaaf; Hans-Jurgen E. Hess, both of Old Lyme, all of Conn.

[73] Assignee: Pfizer Inc., New York, N.Y.

[21] Appl. No.: 249,930

[22] Filed: Apr. 1, 1981

Related U.S. Application Data

[62] Division of Ser. No. 805,879, Jun. 13, 1977, abandoned.

[51] Int. Cl.$^3$ .................... C01D 405/08; A61K 31/4
[52] U.S. Cl. .................................. 542/431; 424/269

[58] Field of Search ............... 548/253, 252; 542/429, 542/431

[56] References Cited

U.S. PATENT DOCUMENTS 3,932,389 1/1976 Johnson et al. .................... 542/429

Primary Examiner—David B. Springer
Attorney, Agent, or Firm—Connolly and Hutz

[57] ABSTRACT

15-Substituted-ω-pentanorprostaglandin C-1 tetrazoles, imides and sulfonimides.

Their use as anti-secretory agents or as agents for the control of fertility.

1 Claim, No Drawings

2-DESCARBOXY-2-(TETRAZOL-5-YL)-16,16-DIMETHYL-17-(2-FURYL)-ω-TRISNORPROSTAGLANDIN E₂

This application is a division of application Ser. No. 805,879 filed June 13, 1977 now abandoned.

BACKGROUND OF THE INVENTION

This invention relates to certain novel analogs of the naturally occurring prostaglandins, synthetic intermediates and processes employed in their preparation. In particular, it relates to novel 2-descarboxy-2-tetrazol-5-yl-15-substituted-ω-pentanorprostaglandins and N-acyl and N-sulfonyl 15-substituted-ω-pentanorprostaglandin carboxamides wherein the 15-substituent is (2-aryl)ethyl or (1,1-dimethyl-2-aryl)ethyl.

The prostaglandins are C-20 unsaturated fatty acids which exhibit diverse physiological effects. Their structure, biological activities and medicinal use have been variously described in U.S. Pat. Nos. 3,971,826 and 3,984,400.

In the preparation of synthetic pharmaceutical agents, among one of the principle objects is the development of analogs of naturally occurring compounds which are highly selective in their physiological activity and which have an increased duration of activity. In a series of compounds like the naturally-occurring prostaglandins which have an extremely broad activity spectrum, increasing the selectivity of a single compound usually involves the enhancement of one physiological effect and the diminution of the others. By increasing the selectivity, one would, in the case of the natural prostaglandins, expect to alleviate the severe side effects, particularly the gastrointestinal effect frequently observed following systemic administration of the natural prostaglandins.

In order to achieve increased selectivity and duration of action in the 11-hydroxy prostaglandin series, many researchers have concentrated on the molecular modification of the last five carbons of the bottom side chain. One modification consists of removing one to four carbon atoms from the end of the lower side chain and terminating the chain with an aryl or heteroaryl group. Compounds of this type are described, for instance, in Belgian Pat. No. 802,231 and in U.S. Pat. No. 3,984,424. Another modification of this portion of the bottom side chain consists of replacing some of the hydrogens attached to the last five carbon atoms with alkyl groups. Compounds of this type are, for instance, 16,16-dimethyl prostaglandin E₂ and F₂α which are described by B. J. Magerkin et al, *Prostaglandins* 4, 143 (1973). Other researchers have concentrated on the molecular modification of the carboxylic acid group at the C-1 position of 11-hydroxy prostaglandins. Several of these modifications consist of converting the carboxylic acid group into an N-acyl or N-sulfonyl carboxamide or into a tetrazole. Compounds of the carboxamide type are described in U.S. Pat. No. 3,954,741 and compounds of the tetrazole type are described in U.S. Pat. No. 3,883,513.

These references describe the biological activities of the 11-hydroxy prostaglandins they disclose as being: hypotensive, bronchodilator, anti-fertility and in some cases anti-ulcer and anti-thrombogenic. Specifically, U.S. Pat. No. 3,984,424 states that the p-biphenyl esters of 17-aryl-ω-trisnorprostaglandins have potent anti-fertility activity.

In view of the prior art and biological tests of the compounds described therein, it has been surprisingly discovered that all members of the instant 15-substituted-ω-pentanor prostaglandins of the F series and the instant 15-substituted-ω-pentanor prostaglandins of the E series wherein the 15-substituted is 2-arylethyl all have potent anti-fertility activity while having diminished hypotensive and diarrheal activity. It further has been discovered that in view of the cited prior art, the instant 15-substituted-ω-pentanor prostaglandins of the E series wherein the 15-substituent is 1,1-dimethyl-2-arylethyl have potent anti-ulcer activity while having diminished hypotensive, diarrheal and smooth muscle activity.

SUMMARY OF THE INVENTION

The present invention comprises prostaglandins that have selective and potent biological activity and includes compounds of the structure:

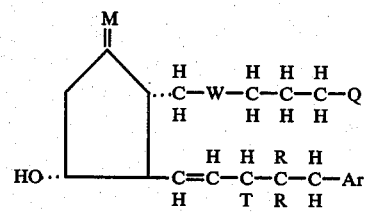

wherein
Ar is phenyl or 2-thienyl, 1- or 2-furyl or monosubstituted phenyl, said substituent being fluoro, chloro, methyl, methoxy trifluoromethyl or phenyl;
each R is the same and is hydrogen or methyl;
Q is tetrazol-5-yl or

R² is alkanoyl having from 2 to 5 carbon atoms, benzoyl or alkylsulfonyl having from 1 to 4 carbon atoms;
W is ethylene or cis-vinylene;
M is oxo or

T is alpha or beta hydroxyl;
provided that when M is

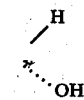

and R is hydrogen, Q is tetrazol-5-yl.

Of interest are the prostaglandins of the present invention wherein Ar is phenyl, R is hydrogen and Q is tetrazol-5-yl, —CONHCOCH₃, or —CONHSO₂CH₃ or wherein Ar is 2-furyl, R is methyl and Q is tetrazol-5-yl, —CONHCOCH₃ or —CONHSO₂CH₃.

Of special interest are 2-descarboxy-2-(tetrazol-5-yl)-17-phenyl-ω-trisnnor PGE₂ and PGF₂; N-acetyl-17-phenyl-ω-trisnor PGE₂ carboxamide; N-methanesulfonyl-17-phenyl-ω-trisnor PGE₂ carboxamide; 2-descarboxy-2-(tetrazol-5-yl)-16,16-dimethyl-17(2-furyl)-ω-trisnnor PGE₂; and PGF$_{2\alpha}$; N-acetyl-16,16-dimethyl-17-(2-furyl)-ω-trisnor PGE₂ carboxamide and PGF$_{2\alpha}$ carboxamide and N-methanesulfonyl-16,16-dimethyl-17-(2-furyl)-ω-trisnor PGE₂ carboxamide and PGF$_{2\alpha}$ carboxamide.

The present invention also comprises the 11,15-bis-(tetrahydropyran-2-yl) PGF$_{2\alpha}$ PGE₂, PGE₁ and PGF$_{1\alpha}$ intermediates used in synthesizing the final product prostaglandins supra.

DETAILED DESCRIPTION OF THE INVENTION

The 15-Substituted-ω-pentanorprostaglandin compounds of the instant invention are prepared by a three-part sequence which is predicated upon the synthesis of the ω or bottom side chain, proceeds to the synthesis of the α or top side chain and ends with the conversion of the synthesized PGF$_{2\alpha}$ intermediate into the array of final products. The sequence, which is presented in Schemes A, B, and C, employs as a starting material the known compound 2-(3α-p-phenylbenzoyloxy-5α-hydroxy-2β-formylcyclopent-1α-yl)acetic acid, α-lactone [E. J. Corey, et al., J. Am. Chem. Soc. 92,387 (1970)] of formula 1.

Scheme A
ω-chain sequence

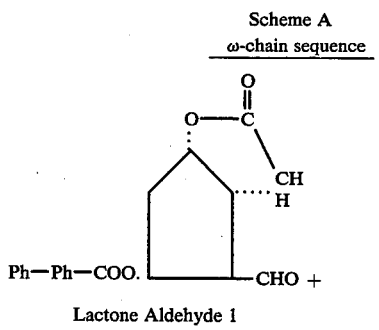

Lactone Aldehyde 1

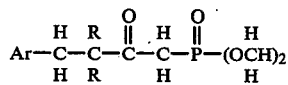

Phosphonate

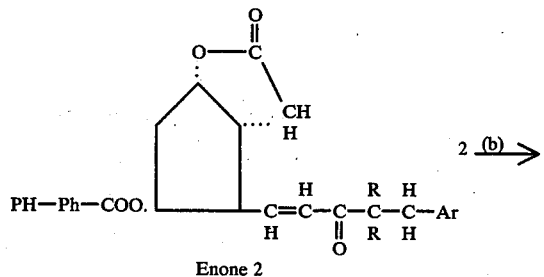

Enone 2

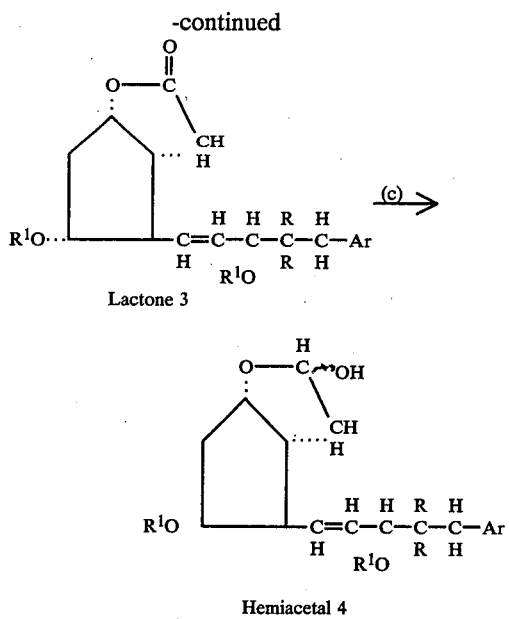

Lactone 3

Hemiacetal 4

R¹ is a mild reagent labile group

The synthetic sequence of Scheme A illustrates the formation of the ω chain. According to reaction (a), the "Lactone Aldehyde" (1) is contacted with the "Phosphonate" wherein R is hydrogen or methyl and Ar is phenyl, thienyl, furyl or monosubstituted phenyl, said substituent being phenyl, fluoro, chloro, methyl, methoxy or trifluoromethyl to form "Enone" 2. Preliminary to this step, however, the "Phosphonate" must be prepared by condensing the appropriate carboxylic acid ester with dimethyl methylphosphonate.

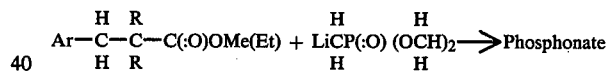

Contact of the lithium salt of dimethylmethylphosphonate with methyl or ethyl 3-aryl propionate or 2,2-dimethylpropionate wherein the aryl group (Ar) is defined supra in solution with ethereal solvents such as tetrahydrofuran or ether at temperatures of −78° to −60° and usually at the temperature of a dry ice/acetone bath for periods ranging from 30 minutes to 120 minutes will produce the "Phosphonate".

It is purified by neutralizing the reaction mixture with an appropriate amount of an organic acid such as acetic acid, followed by isolation using such common techniques as column chromatography and/or distillation.

Reaction (a) is then carried out using the sodium or lithium salt of the "Phosphonate" in combination with the "Lactone Aldehyde" of formula 1 in a "Wadsworth-Emmons" reaction to prepare "Enone" 2. In this procedure, the sodium or lithium salt of the "Phosphonate" is prepared by contact of the "Phosphonat with a base such as sodium hydride or n-butyl lithium in ethereal solvents such as tetrahydrofuran or dimethoxyethane at ambient temperature. Then, this salt is contacted with the "Lactone Aldehyde," formula 1, at temperatures 0° to 30° for about 30 to 90 minutes to form "Enone" 2. The reaction mixture is neutralized with an organic acid and the product is isolated by the usual technique of column chromatography.

The second part of Scheme A, which is represented by step (b), consists of the following reactions: reduction of the enone fragment of "Enone" 2 to an allyl alcohol fragment; transesterification of the p-biphenyl-carboxy group; and the formation of a mild reagent labile ether at each of the hydroxyl positions to produce "Lactone" 3. The reduction of the enone fragment can be accomplished by any reducing agent, which attacks only the carbonyl of the enone fragment. It is usual to employ a trialkylborohydride such as lithium tri-sec-butylborohydride in a stoichiometric ratio to the enone and the reaction is conducted at about dry ice temperature for 30 to 90 minutes in the ethereal solvents followed by neutralization. This reduction produces two compound which are the $\alpha$ and $\beta$ forms of the alcohol at C15. They are diasteromers and are separable by common techniques such as column chromatography and high pressure liquid chromatography. The $\alpha$ or $\beta$ form of the alcohol is then carried on to the final products.

Removal of the p-biphenylester group from the resultant allyl alcohol intermediate supra is accomplished by transesterification in basic alcoholic media. Any weak base which is sufficient to catalyze the transesterification of esters will accomplish the task and the usual reaction conditions are: contact of the ester intermediate with potassium carbonate in methanol for about an hour, neutralization and isolation by extraction.

These two procedures, reduction and transesterification, produce hydroxyl groups at C-11 and C-15 of the prostaglandin intermediate. Conversion of the hydroxyl functions of C-11 and C-15 to mild reagent labile ethers completes step (b) and produces the "Lactone" of formula 3.

Any group which will function as a mild reagent labile protecting group can be employed as the moiety $R^1$. Some groups are tetrahydropyran-2-yl and dimethyl-t-butyl silyl. If tetrahydropyran-2-yl is employed as $R^1$, the method of formation from the C-11, C-15 prostaglandin intermediate diol, as formed supra, usually will employ an excess of 2,3-dihydropyran in methylene chloride with p-toluenesulfonic acid as a catalyst and reaction times of 30 to 90 minutes. Alternatively, the intermediate diol may be contacted with dimethyl-t-butyl silyl chloride in a polar solvent such as dimethylformamide in the presence of imidazole at 50° for 12–24 hours. After following either of these procedures, the product, "Lactone" of formula 3, can be isolated by basic extraction and column chromatography.

The third part of Scheme A is step (c) and consists of the conversion of the lactone group to a hemiacetal group in preparation for the α-chain attachment. Step (c) can be accomplished by using any reducing agent which will convert a lactone group to a hemiacetal (lactol) group. In the usual procedure, "Lactone" 3 is reduced to "Hemiacetal" 4 by contacting it with a stoichiometric amount of diisobutylaluminumhydride at −78° to −60° C. in an inert solvent such as toluene. After it is determined that the reaction is essentially complete, usually through the examination of a thin layer chromatograph of an aliquot of the reaction mixture, the reaction is quenched with a hydroxylic solvent such as methanol and allowed to warm to ambient temperature. The "Hemiacetal" 4 is usually isolated by ethereal solvent/water extraction or trituration with methanol.

Scheme B is the synthesis of the α-chain which will form a prostaglandin of formula 5 by combining the "Hemiacetal" of formula 4 with elements of the "Phosphorane" of formula 11.

Reaction (d) of this scheme is a Wittig reaction of "Phosphorane" 11 with "Hemiacetal" 4. The preparation of "Phosphorane" 11 and the reaction of it with 4 are accomplished in one operation starting from a phosphonium salt of the structure:

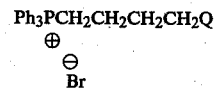

wherein Q is defined supra. This salt in turn is prepared according to the methods as described in U.S. Pat. No. 3,953,466 when Q is tetrazol-5-yl and as described in U.S. Pat No. 3,954,741 when Q is

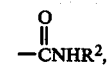

$R^2$ being defined supra.

Scheme B
α-chain sequence

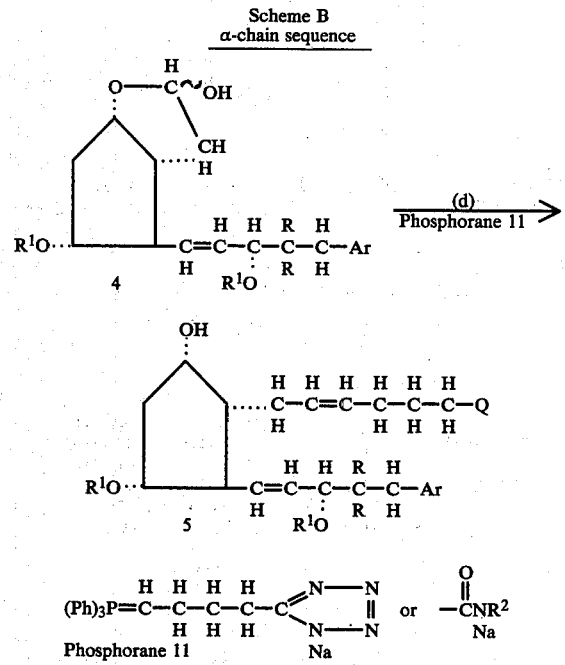

To prepare prostaglandin 5 according to reaction (d), the appropriate phosphonium salt in dimethylsulfoxide is contacted with about two equivalents of sodium methylsulfinylmethide in dimethylsulfoxide at ambient temperature. The resultant solution of "Phosphorane" 11 in dimethylsulfoxide is then contacted with about one third to one fifth molar equivalent of "Hemiacetal" 4 in dimethylsulfoxide at 10° to 40° C. After the reaction is substantially complete, usually about 0.5 to 16 hours, it is neutralized with water and then acid. Prostaglandin 5 is then isolated by common techniques such as column chromatography or high pressure liquid chromatography.

Scheme C
Products of the Invention

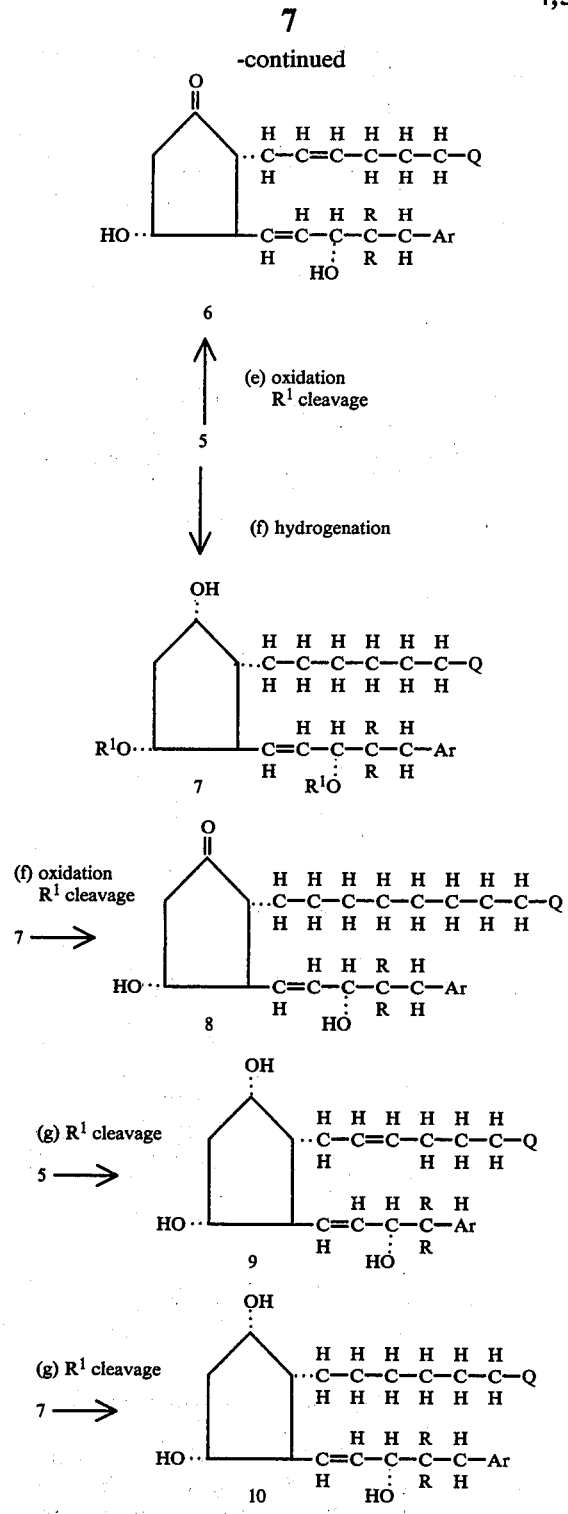

Scheme C shows the conversion of the prostaglandin $F_{2\alpha}$ intermediate 5 to the prostaglandin $F_{1\alpha}$ intermediate 7, the conversion of 5 to both prostaglandin $E_2$ compound 6 and prostaglandin $F_{2\alpha}$ compound 9 and the conversion of 7 to both prostaglandin $E_1$ compound 8 and prostaglandin $F_{1\alpha}$ compound 10. Reaction step (f) of this scheme produces intermediate 7 and is the catalytic hydrogenation of the C5-C6 double bond of intermediate 5. Reaction step (e) produces compounds 6 and 8 and consists of two reactions: Jones oxidation of the C9 hydroxyl to a keto group and the acid cleavage of protecting group $R^1$. Reaction step (g) produces compounds 9 and 10 and is the acid cleavage of protecting group $R^1$.

According to the present invention, the method for the Jones oxidation is contact of intermediate 5 or 7 with Jones reagent (chromium trioxide in sulfuric acid and water) in acetone solution for about 5 minutes at $-20°$ to $0°$ C. followed by quenching with isopropanol. The oxidized intermediate can be either isolated by common techniques such as column chromatography or, preferably used without purification.

The method for cleavage of protecting group $R^1$ is contact of the appropriate intermediate 5 or 7 or the oxidized forms of 5 or 7 described supra with a mixture of acetic acid and water for 5 to 24 hours at $20°$ to $40°$ C.

Alternatively, when $R^1$ is dimethyl-t-butyl silyl, another method for cleavage is contact with tetraalkylammonium fluoride such as tetra-n-butyammonium fluoride in such solvents as tetrahydrofuran or diethoxyethane. The final products 6, 8, 9 or 10 can be isolated by concentration of the reaction mixture followed by use of such common purification techniques as column or high pressure liquid chromatography.

The method for catalytic hydrogenation is agitation of intermediate 5 in methanol, ethanol or ethyl acetate solution with a noble metal catalyst such as palladium on carbon under one atmosphere of hydrogen at $-20°$ C. until one equivalent of hydrogen is absorbed. Isolation of intermediate 7 is then accomplished by removal of catalyst and solvent and optionally by column chromatography.

In numerous in vivo and in vitro tests, it has been established that the prostaglandin compounds of the present invention exhibit extreme selectivity. Their biological achievement is the diminuation of many of the physiological activities of the natural prostaglandins while maintaining activity in one area. The tests which allow such determination of selectivity include among others, a test for effect on isolated smooth muscle for guinea pig and rat uterus, effect on dog blood pressure, inhibition of histamine induced bronchoconstriction in the guinea pig, inhibition of cold, stress-induced ulceration in the rat and diarrheal effect in the mouse.

After comparison to the responses caused by natural prostaglandins in the same tests, the physiological responses caused by the experimental prostaglandin in these tests are helpful in determining its usefulness for the treatment of natural and pathological malconditions. Based upon such comparison, the instant 15-substituted-ω-pentanorprostaglandins of the E series having both R substituents as hydrogen and of the F series having both R substituents as hydrogen or methyl have utility as selective anti-fertility agents and those of the E series having both R substituents as methyl have utility as anti-ulcer agents. These selective utilities are made apparent by the observation of uterine smooth muscle activity for all of the compounds of the F series and those of the E series wherein both R substituents are hydrogen, observation of anti-secretory activity for the compounds of the E series of the present invention wherein both R substituents are methyl and the dimunuation of such determined activities as hypotensive activity, diarrheal activity and bronchodilator activity.

Prime examples of the anti-fertility therapeutic importance with respect to selectivity are 2-descarboxy-2-(tetrazol-5-yl)-17-phenyl-ω-trisnorprostaglandin $E_2$ and 2-descarboxy-2-(tetrazol-5-yl)-17-phenyl-ω-trisnorprostaglandin $F_{2\alpha}$. N-Methylsulfonyl-17-phenyl-ω-trisnorprostaglandin $E_2$ carboxamide, and N-Acetyl-17-phenyl-ω-trisnorprostaglandin $E_2$ carboxamide. While the above $PGE_2$ compounds exhibit potency comparable to natural $PGE_2$ in the rat and guinea pig isolated uterine smooth muscle test, they are a tenth as potent as natural $PGE_2$ in causing diarrhea in the mouse, and also are less potent in inhibiting bronchoconstriction in the histamine aerosol-guinea pig pulmonary test and in reducing blood pressure in dogs. In addition, while they exhibit a potency comparable to 17-phenyl-ω-trinorprostaglandin $E_2$ (acid) and its p-biphenyl ester in the rat and guinea pig isolated uterine smooth muscle test, they are significantly less potent than the said acid and said ester in reducing blood pressure in dogs. Likewise, the above $PGF_{2\alpha}$ compounds exhibit comparable activity to natural $PGE_2$ in the rat isolated uterine smooth muscle test. The methods of these tests are described in U.S. Pat. No. 3,956,284.

Outstanding examples of prostaglandins of the present invention having selective anti-ulcer activity are 2-descarboxy-2-(tetrazol-5-yl)-16,16-dimethyl-17-(2-furyl)-ω-trisnorprostaglandin $E_2$ and N-acetyl and N-methyl sulfonyl-16,16-dimethyl-17-(2-furyl)-ω-trisnorprostaglandin $E_2$ carboxamide. They exhibit activity comparable to natural $PGE_2$ in the dog gastric acid anti-secretory test while showing significantly less activity than natural $PGE_2$ in the guinea pig uterus test.

The new compounds of this invention can be used in a variety of pharmaceutical formulations which contain the compound, or its pharmaceutically acceptable salts. They may be administered in the same manner as natural prostaglandins by a variety of routes, such as intravenous, oral, intravaginal, intra- and extra-amniotic, among others, as anti-fertility agents for the induction of labor, as abortifacients, and as agents having anti-fertility activity through a mechanism not affecting smooth muscle, for example luteolytic mechanisms, and the synchronization of the estrous cycle in farm animals.

For pharmaceutical formulation and for solid compounding of the prostaglandin compounds of the present invention, the useful pharmacological acceptable salts are those with pharmacologically acceptable metal cations, ammonium, amine cations, or quaternary ammonium cations.

Especially preferred metal cations are those derived from the alkali metal, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, benzylamine, α-phenylethylamine, β-phenylethylamine, as well as heterocyclic amines, e.g., piperidine, morpholine, pyrrolidine, and piperazine as well as amines containing water-solubilizing or hydrophilic groups, e.g., mono-, di-, and triethanolamine, ethyldiethanolamine, galactamine, N-methylglucosamine, ephedrine phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparation which contain the compound or a pharmaceutically acceptable salt thereof, and they may be administered by several routes as described above. Although the particular dose, formulation and route of administration are dependent upon each patient's unique condition and the wisdom of his attending physician, the guidelines set forth infra for certain 15-substituted-ω-pentanorprostaglandins of the present invention describe their usefulness as anti-fertility agents and describes the usefulness of others as anti-ulcer agents.

For induction of abortion, the novel 15-substituted-ω-pentanorprostaglandins of all members of the F series and of the E series wherein both R substituents are hydrogen may be orally administered in appropriately formulated tablets, aqueous suspensions or alcoholic solutions containing about 0.1–20 mg., of prostaglandin per dose with 1–7 doses per day being employed. For intravaginal administration a suitable formulation would be lactose tablets or an impregnated tampon containing about 0.1–20 mg of prostaglandin per dose with 1–7 doses being employed. For intra-amniotic administration a suitable formulation would be an aqueous solution containing the prostaglandin at 0.05–10 mg/dose with 1–7 doses being employed. For extra-amniotic administration a suitable formulation would be an aqueous solution containing the prostaglandin at 0.05–1 mg/dose with 1–5 doses being employed. Alternatively, the novel 15-substituted-ω-pentanorprostaglandins of all members of the F series and of the E series wherein both R substituents are hydrogen can be infused intravenously for induction of abortion at doses of 0.05–50 g of prostaglandin per minute for a period of from about 1–24 hours.

Another use for the novel 15-substituted-ω-pentanorprostaglandins of all members of the F series and the E series wherein both R substituents are hydrogen is an inducer of labor. For this purpose an ethanol-saline solution of the prostaglandins is employed for an intravenous infusion in the amount of from about 0.1–10 μg/kg/min of prostaglandin for about 1–24 hours.

Another use for the novel 15-substituted-ω-pentanorprostaglandin compounds of all members of the F series and of the E series wherein both R substituents are hydrogen is fertility control. For this purpose a tablet is employed for intravaginal or oral administration containing 0.1–20 mg of prostaglandin per dose with 1–7 doses being employed at or following the expected day of menstruation. For synchronization of the estrous cycle in pigs, sheep, cows or horses, a solution or suspension containing 0.03–30 mg/dose of the prostaglandin administered subcutaneously or intramuscularly from 1–4 days.

15-substituted-ω-pentanorprostaglandins of the E series of the present invention having both R substituents as methyl are useful as anti-ulcer agents. For treatment of peptic ulcers, these drugs are appropriately administered orally in the form of aqueous suspensions, ethanolic solutions or preferably in the form of capsules or tablets containing 0.001 to 0.10 mg/kg of prostaglandin per dose with up to 12 doses per day.

To prepare any of the above dosage forms or any of the numerous other forms possible, various reaction-inert diluents, excipients or carriers may be employed. Such substances include, for example, water, ethanol, gelatins, lactose, starches magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. The spectral data were obtained on a Varian T-60 or an A-60 NMR and a Perkin-Elmer Grating Infrared Spectrometer. The infrared data are given in microns and the NMR data are given in parts per million using TMS as a standard. Melting points are uncorrected and are in °Centigrade.

In general, the temperatures of the reactions described in the examples, when unspecified, will be taken to mean ambient or room temperature which varies from 15° to 30° C.

The time requirements of the reactions described in the examples, unless otherwise stated, were determined by monitoring with thin layer chromatography (TLC). The usual TLC system was silica-gel on glass (E. Merck-Silica Gel plates, E. Merck, Dormstadt, W. Germany) with benzene/ether or methanol, chloroform as eluants ad vanillin/ethanol or iodine as developers. ["Introduction to Chromatography" J. M. Bobbitt, A. E. Schwarting, R. J. Gritter, Van Nostrand-Reinhold, N.Y. 1968]. As a general rule, the reaction in question was deemed essentially complete when the TLC spot representing the critical starting material had disappeared or had quit changing in appearance.

EXAMPLE 1

2-[3α-p-Phenylbenzoyloxy-5α-hydroxy-2β-(3-oxo-5-phenyl-trans-1-penten-1-yl)cyclopent-1α-yl]Acetic Acid, γ-lactone (14)

To a suspension of 1.32 g. (31.5 mmoles) of sodium hydride (56.6% dispersion in mineral oil) in 400 ml. of 1.2 dimethoxyethane was added 8.80 g. (34.4 mmoles) of dimethyl 2-oxo-4-phenyl butyl phosphonate (13) dropwise. The heterogeneous mixture was stirred at room temperature for 25 minutes, heated at reflux for 1 hour then let cool to room temperature. A suspension of 10.0 g. (28.6 mmole) of 2-[3α-p-phenylbenzoyloxy-5α-hydroxy-2β-formylcyclopentan-1α-yl]acetic acid, γ-lactone in 80 ml. of 1,2-dimethoxyethane was added and the mixture was stirred for 45 minutes, was neutralized with and concentrated. The crude mixture was dissolved in methylene chloride, glacial acetic acid, washed with 50 ml. water and 50 ml. saturated bringe dried (MgSO₄) and evaporated to yield 7.47 g. (55%) 2-[3α-p-phenyl-benzoyloxy-5α-hydroxy-2β-(3-oxo-5-phenyl-trans-1-penten-1-yl)-cyclopent-1α-yl]acetic acid, γ-lactone (14) as a white solid (m.p. 127°-129° from methylene chloride-hexane.

In addition the other Enone intermediates of the present invention having the structure of Enone 2 above may be prepared using the procedure of Example 1 by substituting for phosphonate 13 in Example 1 the appropriate phosphonate having the structure

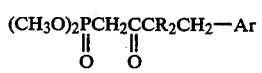

wherein R and Ar are as defined above.

EXAMPLE 2

2-[3α-p-phenylbenzoyloxy-5α-hydroxy-2β-(3α-hydroxy-5-phenyl-trans-1-penten-yl]cyclopent-1α-yl]acetic acid, γ-lactone (15) and 2-[3α-p-phenylbenzoyloxy-5α-hydroxy-2β-(3β-hydroxy-5-phenyl-trans-1-penten-1-yl]cyclopent-1α-yl]acetic acid γ-lactone (16)

To a solution of 7.0 g. (14.6 mmole) of 2-(3α-p-phenylbenzyloxy-5α-hydroxy-2β-(3-oxo-5-phenyl-trans-1-penten-1-yl)cyclopent-1α-yl]acetic acid, γ-lactone (14) in 150 ml. of tetrahydrofuran, cooled to −78° C., was added 30 ml. of a solution of lithium tri-sec-butylborohydride in tetrahydrofuran in portions until the reaction was complete by tlc. The solution is then quenched in the cold by the addition of 100 ml. of a 60:40 mixture of water:acetic acid. The quenched mixture is let warm then extracted with methylene chloride (3×150 ml.). The combined organic extract were washed with water (50 ml.) and saturated brine (50 ml.) were dried (anhydrous magnesium sulfate) and concentrated. Purification of the crude product by silica gel column chromatography using a 9:1 mixture of ether:-cyclohexane as eluent provided the desired 2-[3α-p-phenylbenzoyloxy-5α-hydroxy-2β-(3α-hydroxy-5-phenyl-trans-1-penten-1-yl)cyclopent-1α-yl]acetic acid, γ-lactone (15) as a white form weighed 3.72 g. (53.2% yield). Elution with ethyl acetate provided 2-[3α-p-phenylbenzoyloxy-5α-hydroxy-2β-(3β-hydroxy-5-phenyl-trans-1-penten-1-yl)cyclopent-1α-yl]acetic acid, lactone (16) as an oil weighing 2.15 g. (34.7% yield).

In addition, the other reduced Enone intermediates of the present invention may be prepared by the procedure of Example 2 by substituting the appropriate Enone intermediate prepared according to Example 1 for Enone 14 in Example 2.

EXAMPLE 3

2-[3α,5α-dihydroxy-2β-(3α-hydroxy-5-phenyl-trans-1-penten-1-yl)cyclopent-1α-yl]acetic acid, γ-lactone (17)

A heterogenous mixture of 3.72 g. (1.35 mmole) of 2-[3α-p-phenylbenzoyloxy-5α-hydroxy-2β-(3α-hydroxy-5-phenyl-trans-1-penten-1-yl)cyclopent-1α-yl]acetic acid, γ-lactone (15), 37 ml. of absolute methanol, 20 ml. of tetrahydrofuran and 1.07 g. (7.72 mmoles) of finely powdered, anhydrous potassium carbonate was stirred at room temperature for 1.25 hour, then cooled to 0° C. To the cooled solution was added 15.4 ml. (15.4 mmole) of 1.0 N aqueous hydrochloric acid and 57 ml. of water with concomitant formation of methyl p-phenylbenzoate which was collected by filtration. The filtrate was extracted with acetate, (3×50 ml.), the combined organic extracts were washed with saturated sodium chloride (10 ml.), dried (MgSO₂) and concentrated to give 2.28 g. (97.5% yield) of viscous, oily 2-[3α,5α-dihydroxy-2β-(3α-hydroxy-5-phenyl-trans-1-penten-yl)cyclopent-1α-yl]acetic acid, γ-lactone (17).

In addition the other dihydroxy Lactone intermediates of the present invention may be prepared by the procedure of Example 3 by substituting the appropriate reduced Enone intermediate prepared according to Example 2 for lactone 15 in Example 3.

EXAMPLE 4

2-[5α-hydroxy-3α-(tetrahydropyran-2-yloxy)-2β-(3α-[tetrahydropyran-2-yloxy]-5-phenyl-trans-1-penten-1-yl)cyclopent-1α-yl]acetic acid, γ-lactone (18)

To a solution of 2.28 g. (7.55 mmole) 2-[3α,5α-dihydroxy-2β-(3α-hydroxy-4-phenyl-trans-1-penten-yl)cyclopent-1α-yl]acetic acid γ-lactone (17) in 23 ml. anhydrous methylene chloride and 2.3 ml. of distilled 2,3-dihydropyran in a dry nitrogen atmosphere was added 23 mg. p-toluenesulfonic acid monohydrate. After being stirred for 2 hours, the reaction mixture was combined with 230 ml. ether, the organic solution was washed with saturated sodium bicarbonate (30 ml.), dried (MgSO$_4$) and concentrated to yield 3.61 g. (100%) crude 2-[5α-hydroxy-3α-(tetrahydropyran-2-yloxy)-2β-(3α-[tetrahydropyran-2-yloxy]-5-phenyl-trans-1-penten-1-yl)cyclopent-1α-yl]acetic acid, γ-lactone (18) as an oil.

In addition the other bis THP lactone intermediates of the present invention may be prepared by the procedure of Example 4 by substituting the appropriate dihydroxy lactone intermediate prepared according to Example 3 for dihydroxy lactone 17 in Example 4.

EXAMPLE 5

2-[5α-hydroxy-3α-(tetrahydropyran-2-yloxy)-2β-(3α-[tetrahydropyran-2-yloxy]-5-phenyl-trans-1-penten-1-yl)cyclopent-1α-yl]acetaldehyde, γ-hemiacetal (19)

A solution of 3.61 g. (assumed to be 7.55 mmole) 2-[5α-hydroxy-3α-(tetrahydropyran-2-yloxy)-2β-(3α-[tetrahydropyran-2-yloxy]-5-phenyl-trans-1-penten-1-yl)cyclopent-1α-yl]acetic acid, γ-lactone (18) in 50 ml. dry toluene was cooled at −78° in a dry nitrogen atmosphere. To this cooled solution was added 10.3 ml. (8.30 mmole) of a 20% solution of diisobutylaluminum hydride in n-hexane dropwise at such a rate so that the internal temperature never rose above −65° (5 minutes) After an additional 2 hours at −78°, anhydrous methanol was added the reaction mixture was allowed to warm to room temperature was concentrated. The crude product was diluted with 150 ml. of methanol, the insoluble material collected by filtration, and the filtrate concentrated. Purification of the crude product by silica gel column chromatography using mixtures of benzene-ethyl acetate as eluents provided, after removal of less polar impurities the oily 2-[5α-hydroxy-3α-(tetrahydropyran-2-yloxy)-2β-(3α-[tetrahydropyran-2-yloxy]-5-phenyl-trans-1-penten-1-yl)-cyclopent-1α-yl]acetaldehyde, γ-hemiacetal (19) weighing 3.04 g. (86% yield).

In addition the other hemiacetal intermediates of the present invention may be prepared by the procedure of Example 5 by substituting the appropriate bis THP lactone intermediate prepared according to Example 4 for bis THP lactone 18 in Example 5.

EXAMPLE 6

5α-hydroxy-3α-(tetrahydropyran-2-yloxy)-2β-[3α-(tetrahydropyran-2-yloxy)-5-phenyl-trans-1-penten-1-yl]-1α-[6-(tetrazol-5-yl)-cis-2-hexen-1-yl]cyclopentane (1)

To a solution of 2.92 g (6.3 mmole) [4-(tetrazol-5-yl)-n-butyl]triphenylphosphonium bromide in a dry nitrogen atmosphere on 6.0 ml dry dimethyl sulfoxide was added 8.02 ml (12.1 mmole) of a 1.51 M solution of sodium methylsulfinylmethide in dimethyl sulfoxide. To this red ylide solution was added dropwise a solution of 1.0 g (2.11 mmole) 2-[5α-hydroxy-3α-(tetrahydropyran-2-yloxy)-2β-(3α-(tetrahydropyran-2-yloxy)-5-phenyl-trans-1-penten-1-yl)cyclopent-1α-yl]acetaldehyde, γ-hemiacetal (19) in 2.0 ml dry dimethyl sulfoxide over a period of 20 minutes. After an additional 1.5 hours stirring at room temperature, the reaction mixture was poured onto ice water. The basic aqueous solution was acidified to ca. pH 3 with 10% aqueous hydrochloric acid. The acidic solution was extracted with ethyl acetate (3×20 ml) and the combined organic extracts washed once with water (10 ml.), dried (MgSO$_4$) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high R$_f$ impurities, the desired 5α-hydroxy-3α-(tetrahydropyran-2-yloxy)-2β-[3α-(tetrahydropyran-2-yloxy]-5-phenyl-trans-1-penten-1-yl]-1α-[6-(tetrazol-5-yl)-cis-2-hexen-1-yl]cyclopentane (1) was collected as a colorless oil weighing 1.19 g (97.2% yield).

In addition the other 2-descarboxy-2-(tetrazol-5-yl)-11,15-bis(tetrahydropyran-2-yl) PGF$_{2\alpha}$ intermediates of the present invention may be prepared by the procedure of Example 6 by substituting the appropriate hemiacetal intermediate prepared according to Example 5 for the hemiacetal (19) in Example 6.

EXAMPLE 7

3α,5α,-Dihydroxy-2β-[3α-hydroxy-5-phenyl-trans-1-penten-1-yl]-1α-[6-(tetrazol-5-yl)-cis-2-hexen-1-yl]cyclopentane (2)

A solution of 300 mg. (0.69 mmole) 5α-hydroxy-3α-(tetrahydropyran-2-yloxy)-2β-[3α-(tetrahydropyran-2-yloxy)-5-phenyl-trans-1-penten-1-yl]-1α-[6-(tetrazol-5-yl)-cis-2-hexen-1-yl]cyclopentane (1) in 6.0 ml of 65:35 mixture of glacial acetic acid-water was stirred under nitrogen at 25° C. for 18 hours then was concentrated by rotary evaporation. The resultant crude oil was purified by column chromatography on silica gel (Mallinckrodt CC-7 100–200 mesh) using mixtures of chloroform:ethyl acetate as eluent. After elution of less polar impurities the colorless, oily 3α,5α-dihydroxy-2β-[3α-hydroxy-5-phenyl-trans-1-penten-1-yl]-1α-[6-(tetrazol-5-yl)-cis-2-hexen-1-yl]cyclopentane (2) weighing 235 mg (82.8% yield) was collected.

In addition the other 2-descarboxy-2-tetrazol-5-yl PGF$_{2\alpha}$ compounds of the present invention may be prepared by the methods of Example 7 by substituting the appropriate 2-descarboxy-2-tetrazol-5-yl-11,15-bis-(tetrahydropyran-2-yl) PGF$_{2\alpha}$ intermediate prepared according to Example 6 for the PGF$_{2\alpha}$ intermediate (1) in Example 7.

EXAMPLE 8

4α-(tetrahydropyran-2-yloxy)-2α-[6-(tetrazol-5-yl)-cis-2-hexen-1-yl]-3β-[3α-(tetrahydropyran-2-yloxy)-5-phenyl-trans-1-penten-1-yl]cyclopentanone (3)

To a solution cooled to −15° under nitrogen, of 645 mg (1.11 mmole) 5α-hydroxy-3α-(tetrahydropyran-2-yloxy)-2β-[3α-(tetrahydropyran-2-yloxy)-5-phenyl-trans-1-penten-1-yl]-1α-[6-(tetrazol-5-yl)-cis-2-hexen-1-yl]cyclopentane (1) in 12 ml reagent grade acetone was added dropwise 0.63 ml of Jones' reagent. After 30 minutes at −10°, 0.63 ml. 2-propanol was added and the reaction mixture was allowed to stir an additional 5 minutes at which time it was combined with 75 ml. ethyl acetate, washed with water (3×10 ml.), dried (MgSO$_4$) and concentrated to give 542 mg (84% yield) of the colorless, oily 4α-(tetrahydropyran-2-yloxy)-2α-[6-(tetrazol-5-yl)-cis-2-hexen-1-yl]-3β-[3α-(tetrahydropyran-2-yloxy)-5-phenyl-trans-1-penten-1-yl]cyclopentanone (3).

EXAMPLE 9

4α-Hydroxy-2α-[6-(tetrazol-5-yl)-cis-2-hexen-1-yl]-3β-(3α-hydroxy-5-phenyl-trans-1-penten-1-yl)cyclopentanone (4)

A solution of 542 mg. (0.93 mmole) 4α-(tetrahydropyran-2-yloxy)-2α-[6-(tetrazol-5-yl)-cis-2-hexen-1-yl]-3β-[3α-(tetrahydropyran-2-yloxy)-5-phenyl-trans-1-penten-1-yl]cyclopentanone (3) in 10 ml. of 65:35 mixture of glacial acetic acid:water was stirred under nitrogen at 25° for 20 hours then was concentrated by rotary evaporation. The resultant crude oil was purified by column chromatography on silica gel (Mallinckrodt CC-7 100–200 mesh) using mixtures of chloroform:ethyl acetate as eluents. After elution of less polar impurities the crystalline 4α-hydroxy-2α-[6-(tetrazol-5-yl)-cis-2-hexen-1-yl]-3β-(3α-hydroxy-5-phenyl-trans-1-penten-1-yl)cyclopentanone (4) weighing 210 mg (54.4% yield) melting at 93°–96° from ethyl acetate/cyclohexane was collected.

In addition the other 2-descarboxy-2-tetrazol-5-yl PGE$_2$ compounds of the present invention may be prepared by the methods of Examples 8 and 9 by substituting the appropriate 2-descarboxy-2-(tetrazol-5-yl)-11,15-bis(tetrahydropyran-2-yl) PGF$_{2\alpha}$ intermediate prepared according to Example 6 for compound (1) in Example 8.

EXAMPLE 10

N-methanesulfonyl 9α-hydroxy-11α,15α-bis-(tetrahydropyran-2-yloxy)-5-cis-13-trans-17-phenyl-ω-trisnorprostadienamide (5)

To a solution of 3.3 g. (6.3 mmole) [4-(methanesulfonylaminocarbonyl)-n-butyl]triphenylphosphonium bromide in a dry nitrogen atmosphere in 6.0 ml. dry dimethyl sulfoxide was added 6.08 ml. (12.2 mmole) of a 2.05 M solution of sodium methylsulfinylmethide in dimethyl sulfoxide. To this red ylide solution was added dropwise a solution of 900 mg. (2.06 mmole) 2-[5α-hydroxy-3α-(tetrahydropyran-2-yloxy)-2β-(3α-[tetrahydropyran-2-yloxy]-5-phenyl-trans-1-penten-1-yl)cyclopent-1α-yl]-acetaldehyde, γ-hemiacetal (19) in 2.0 ml. dry dimethyl sulfoxide over a period of 20 minutes. After an additional 18 hours stirring at room temperature, the reaction mixture was poured onto ice water. The basic aqueous solution was acidified to pH 3 with 10% aqueous hydrochloric acid. The acidic solution was extracted with ethyl acetate (3×20 ml.) and the combined organic extracts washed once with water (10 ml.), dried (MgSO$_4$) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high R$_f$impurities, the desired N-methanesulfonyl 9α-hydroxy-11α,15α-bis-(tetrahydropyran-2-yloxy)-5-cis-13-trans-17-phenyl-ω-trisnorprostadienamide (5) was collected as a colorless oil weighing 924 mg. (71.0% yield).

In addition the other N-alkylsulfonyl 11,15-bis(THP) PGF$_{2\alpha}$ carboxamides intermediates of the present invention may be synthesized by the method of Example 10 by substituting the appropriate N-alkylsulfonyl phosphonium salt for the N-methanesulfonyl phosphonium salt in Example 10 and by substituting the appropriate hemiacetal intermediate from Example 5 for hemiacetal (19) in Example 10.

EXAMPLE 11

N-methanesulfonyl 9α,11α,15α-trihydroxy-5-cis-13-trans-17-phenyl-ω-trisnorprostadienamide (6)

A solution of 427 mg. (0.67 mmole) N-methanesulfonyl 9α-hydroxy-11α,15α-bis-(tetrahydropyran-2-yloxy)-5-cis-13-trans-17-phenyl-ω-trisnorprostadienamide (5) in 10.0 ml. of a 65:35 mixture of glacial acetic acid:water was stirred under nitrogen at 25° for 18 hours then was concentrated by rotary evaporation. The resultant crude oil was purified by column chromatography on silica gel (Mallinckrodt CC-7 100-200 mesh) using mixtures of chloroform:ethyl acetate as eluent. After elution of less polar impurities the colorless, crystalline N-methanesulfonyl 9α,11α,15α-trihydroxy-5-cis-13-trans-17-phenyl-ω-trisnorprostadienamide (6) weighing 149 mg. (48.0% yield) was collected which melted at 102°-104° from ethyl acetate:hexane.

In addition the other N-alkylsulfonyl PGF$_{2\alpha}$ carboxamides of the present invention may be synthesized by the method of Example 11 by substituting the appropriate N-alkylsulfonyl-11,15-bis(THP) PGF$_{2\alpha}$ carboxamide intermediate from Example 10 for compound (5) in Example 11.

EXAMPLE 12

N-methanesulfonyl 9-oxo-11α,15α-bis-(tetrahydropyran-2-yloxy)-5-cis-13-trans-17-phenyl-ω-trisnorprostadienamide (7):

To a solution cooled to −15° under nitrogen, of 487 mg. (0.77) mmole N-methanesulfonyl 9α-hydroxy-11α,15αbis-(tetrahydropyran-2-yloxy)-5-cis-13-trans-17-phenyl-ω-trisnorprostadienamide (5) in 15 ml. reagent grade acetone was added dropwise 0.45 ml. of Jones' reagent. After 30 minutes at −10°, 0.45 ml. 2-propanol was added and the reaction mixture was allowed to stir an additional 5 minutes at which time it was combined with 75 ml. ethyl acetate, washed with water (3×10 ml.), dried (MgSO$_4$) and concentrated to give 480 mg. (98.5% yield) of the colorless, oily N-methanesulfonyl 9-oxo-11α,15α-bis-(tetrahydropyran-2-yloxy)-5-cis-13-trans-17-phenyl-ω-trisnorprostadienamide (7).

EXAMPLE 13

N-methanesulfonyl 9-oxo-11α,15α-dihydroxy-5-cis-13-trans-17-phenyl ω-trisnorprostadienamide (8)

A solution of 480 mg. (0.76 mmole) N-methanesulfonyl 9-oxo-11α,15α-bis-(tetrahydropyran-2-yloxy)-5-cis-13-trans-17-phenyl-ω-trisnorprostadienamide (7) in 15 ml. of a 65:35 mixture of glacial acetic acid:water was stirred under nitrogen at 25° for 20 hours then was concentrated by rotary evaporation. The resultant crude oil was purified by column chromatography on silica gel (Mallinckrodt CC-7 100–200 mesh) using mixtures of chloroform: ethyl acetate as eluents. After elution of less polar impurities the crystalline N-methanesulfonyl 9-oxo-11α,15α-dihydroxy-5-cis-13- trans-17-phenyl-ω-trisnorprostadienamide (8) weighing 182 mg. (51.8% yield) melting at 125°–125.5° from ethyl acetate:hexane was collected.

In addition the other N-alkylsulfonyl PGE$_2$ carboxamides of the present invention may be synthesized according to the methods of Examples 12 and 13 by substituting the appropriate N-alkylsulfonyl-11,15-bis(THP) PGF$_{2\alpha}$ carboxamide intermediate from Example 10 for compound (5) in Example 12.

EXAMPLE 14

N-acetyl
9α-hydroxy-11α,15α-bis-(tetrahydropyran-2-yloxy)-5-cis-13-trans-17-phenyl-ω-trisnorprostadienamide (9)

To a solution of 3.02 g. (6.3 mmole) [4-(acetylaminocarbonyl)-n-butyl]triphenylphosphonium bromide in a dry nitrogen atmosphere in 6.0 ml. dry dimethyl sulfoxide was added 6.08 ml. (12.2 mmole) of a 2.05 M solution of sodium methylsulfinylmethide in dimethyl sulfoxide. To this red ylide solution was added dropwise a solution of 900 mg. (2.06 mmole) 2-[5α-hydroxy-3α-(tetrahydropyran-2-yloxy)-2β-(3α-[tetrahydropyran-2-yloxy]-5-phenyl-trans-1-penten-1-yl)cyclopent-1α-yl]acetaldehyde, α-hemiacetal (19) in 2.0 ml. dry dimethyl sulfoxide over a period of 20 minutes. After an additional 18 hours stirring at room temperature, the reaction mixture was poured onto ice water. The basic aqueous solution was acidified to ca. pH 3 with 10% aqueous hydrochloric acid. The acidic solution was extracted with ethyl acetate (3×20 ml.) and the combined organic extracts washed once with water (10 ml.), dried (MgSO$_4$) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high R$_f$ impurities, the desired N-acetyl 9α-hydroxy-11α,15α-bis-(tetrahydropyran-2-yloxy)-5-cis-13-trans-17-phenyl-ω-trisnorprostadienamide (9) was collected as a colorless oil 800 mg. (65.0% yield).

In addition the other N-alkanoyl or N-benzoyl 11,15-bis(THP) PGF$_{2\alpha}$ carboxamides intermediates of the present invention may be synthesized by the method of Example 14 by substituting the appropriate N-alkanoyl or N-benzoyl phosphonium salt for the N-acetyl phosphonium salt of Example 14 and by substituting the appropriate hemiacetal intermediate from Example 5 for hemiacetal (19) in Example 14.

EXAMPLE 15

N-acetyl
9α,11α,15α-trihydroxy-5-cis-13-trans-17-phenyl-ω-trisnorprostadienamide (10)

A solution of 179 mg. (0.30 mmole) N-acetyl 9α-hydroxy-11α, 15α-bis-(tetrahydropyran-2-yloxy)-5-bis-13-trans-17-phenyl-ω-trisnorprostadienamide (9) in 6.0 ml. of a 65:35 mixture of glacial acetic acid:water was stirred under nitrogen at 25° for 18 hours then was concentrated by rotary evaporation. The resultant crude oil was purified by column chromatography on silica gel (Mallinckrodt CC-7 100–200 mesh) using mixtures of chloroform: ethyl acetate as eluents. After elution of less polar impurities the colorless, crystalline N-acetyl 9α,11α,15α-trihydroxy-5-cis-13-trans-17-phenyl-ω-trisnorprostadienamide (10) weighing 75 mg. (58.3% yield) was collected which melted at 97°–97.5° from ethyl acetate:hexane.

In addition the other N-alkanoyl or N-benzoyl PGF$_{2\alpha}$ carboxamides of the present invention may be synthesized according to the method of Example 15 by substituting the appropriate N-alkanoyl or N-benzoyl-11,15-bis(THP) PGF$_{2\alpha}$ carboxamide intermediate from Example 14 for compound (9) of Example 15.

EXAMPLE 16

N-acetyl
9-oxo-11α,15α-bis-(tetrahydropyran-2-yloxy)-5-cis-13-trans-17-phenyl-ω-trisnorprostadienamide (11)

To a solution cooled at $-15°$ under nitrogen, of 202 mg. (0.34 mmole) N-acetyl-9α-hydroxy-11α,15α-bis-(tetrahydropyran-2-yloxy)-5-cis-13-trans-17-phenyl-ω-trisnorprostadienamide (9) in 10 ml. reagent grade acetone was added dropwise 0.20 ml. of Jones' reagent. After 30 minutes at $-10°$, 0.20 ml. 2-propanol was added and the reaction mixture was allowed to stir an additional 5 minutes at which time it was combined with 75 ml. ethyl acetate, washed with water (3×10 ml.), dried (MgSO$_4$) and concentrated to give 185 mg. (91.4% yield) of the colorless, oily N-acetyl-9-oxo-11α,15α-bis-(tetrahydropyran-2-yloxy)-5-cis-13-trans-17-phenyl-ω-trisnorprostadienamide (11).

EXAMPLE 17

N-acetyl
9-oxo-11α,15α-dihydroxy-5-cis-13-trans-17-phenyl-ω-trisnorprostadienamide (12)

A solution of 185 mg. (0.31 mmole) N-acetyl 9-oxo-11α,15α-bis-(tetrahydropyran-2-yloxy)-5-cis-13-trans-17-phenyl-ω-trisnorprostadienamide (11) in 10 ml. of a 65:35 mixture of glacial acetic acid:water was stirred under nitrogen at 25° for 20 hours then was concentrated by rotary evaporation. The resultant crude oil was purified by column chromatography on silica gel (Mallinckrodt CC-7 100–200 mesh) using mixtures of chloroform: ethyl acetate as eluents. After elution of less polar impurities the crystalline N-acetyl 9-oxo-11α,15α-dihydroxy-5-cis-13-trans-17-phenyl-ω-trisnorprostadienamide (12) weighing 71 mg. (55.4% yield) melting at 89°–91° for ethyl acetate/cyclohexane was collected.

In addition the other N-alkanoyl or N-benzoyl PGE$_2$ carboxamides of the present invention may be synthesized according to the methods of Examples 16 and 17 by substituting the appropriate N-alkanoyl or N-benzoyl-11,15-bis(THP) PGF$_{2\alpha}$ carboxamide intermediate from Example 14 for compound (9) in Example 16.

EXAMPLE 18

2-[3α,5α-dihydroxy-2β-(3α-hydroxy-4,4-dimethyl-5-(2-furyl)trans-1-penten-yl)cyclopent-1α-yl]acetic acid, γ-lactone (21)

By substituting 15.4 g. (56.2 mmoles) of dimethyl 2-oxo-3,3-dimethyl-4-(2-furyl)butylphosphonate 20 for dimethyl 2-oxo-4-phenylbutylphosphonate 13 in Example 1 using 12.5 g (4.70 mmoles) of the lactone starting material of Example 1 and following the procedures of Example 1, 2 and 3, 4.08 g. (67%) of the desired 2-[3α,5α-dihydroxy-2β-(3α-hydroxy-4,4-dimethyl-5-(2-furyl)-trans-1-penten-1-yl)cyclopent-1α-yl]acetic acid, γ-lactone 21 was prepared.

EXAMPLE 19

2-[5α-hydroxy-3α-(tetrahydropyran-2-yloxy)-2β-(3α-(tetrahydropyran-2-yloxy)-4,4-dimethyl-5-(2-furyl)-trans-1-penten-yl)cyclopent-1α-yl]acetaldehyde, γ-hemiacetal (22)

By substituting 4.08 g. of 2-[3α,5α-dihydroxy-2β-(3α-hydroxy-4,4-dimethyl-5-(2-furyl)-trans-1-penten-1-yl)cyclopent-1α-yl]acetic acid, γ-lactone 21 for the dihydroxy lactone starting material 17 in Example 4 and following the procedures of Example 4 and 5, 5.0 g. (77%) of the desired 2-[5α-hydroxy-3α-(tetrahydropyran-2-yloxy)-2β-(3α-(tetrahydropyran-2-yloxy)-4,4-dimethyl-5-(2-furyl)-trans-1-penten-1-yl)cyclopent-1α-yl]acetaldehyde, γ-hemiacetal 22 was prepared.

EXAMPLE 20

5α-hydroxy-3α-(tetrahydropyran-2-yloxy)-2β-[3α-(tetrahydropyran-2-yloxy)-4,4-dimethyl-5-(2-furyl)-trans-1-penten-1-yl]-1α-[6-(tetrazol-5-yl)-cis-2-hexen-1-yl]cyclopentane (23)

To a solution of 3.50 g. (7.5 mmole) [4-(tetrazol-5-yl)-n-butyl]triphenylphosphonium bromide in a dry nitrogen atmosphere in 7.0 ml. dry dimethyl sulfoxide was added 7.75 ml. (14.5 mmole) of a 1.87 M solution of sodium methylsulfinylmethide in dimethyl sulfoxide. To this red ylide solution was added dropwise a solution of 1.22 g. (2.50 mmole) 2-[5α-hydroxy-3α-(tetrahydropyran-2-yloxy)-2β-(3α-(tetrahydropyran-2-yloxy)-4,4-dimethyl-5-(2-furyl)-1-trans-1-penten-1-yl)cyclopent-1α-yl]acetaldehyde, γ-hemiacetal (22) in 2.0 ml. dry dimethyl sulfoxide over a period of 20 minutes. After an additional 18 hours stirring at room temperature, the reaction mixture was poured onto ice water. The basic aqueous solution was acidified to ca. pH 3 with 10% aqueous hydrochloric acid. The acidic solution was extracted with ethyl acetate (3×20 ml.) and the combined organic extracts washed once with water (10 ml.), dried (MgSO₄) and evaporated to a solid residue. This solid residue was triturated with ether and filtered. The filtrate was purified by column chromatography on silica gel (Baker "Analyzed" Reagent 60–200 mesh) using mixtures of chloroform:ethyl acetate as eluents. After removal of high $R_f$ impurities, the desired 5α-hydroxy-3α-(tetrahydropyran-2-yloxy)-2β-[3α-(tetrahydropyran-2-yloxy)-4,4-dimethyl-5-(2-furyl)-trans-1-penten-1-yl]-1α-[6-(tetrazol-5-yl)-cis-2-hexen-1-yl]cyclopentane (23) was collected as a colorless oil weighting 1.13 g. (83.5% yield).

EXAMPLE 21

3α,5α,-dihydroxy-2β-[3α-hydroxy-4,4-dimethyl-5-(2-furyl)trans-1-penten-1-yl]-1α-6-(tetrazol-5-yl)-cis-2-hexen-1-yl]cyclopentane (24)

A solution of 45.1 mg. (0.84 mmole) 5α-hydroxy-3α (tetrahydropyran-2-yloxy)-2β-[3α-(tetrahydropyran-2-yloxy)-4,4-dimethyl-5-(2-furyl)-trans-1-penten-1-yl]-1α-[6-(tetrazol-5-yl)-cis-2-hexen-1-yl]cyclopentane (23) in 10.0 ml. of 65:35 mixture of glacial acetic acid-water was stirred under nitrogen at 25° for 18 hours then was concentrated by rotary evaporation. The resultant crude oil was purified by column chromatography on silica gel 100-200 SAE mesh) using mixtures of chloroform:ethyl acetate as eluent. After elution of less polar impurities the colorless, oily 3α,5α-dihydroxy-2β-[3α-hydroxy)-4,4-dimethyl-5-(2-furyl)-trans-1-penten-1-yl]-1α-[6-(tetrazol-5-yl)-cis-2-hexen-1-yl]cyclopentane (24) weighing 89 mg. was collected.

EXAMPLE 22

4α-(tetrahydropyran-2-yloxy)-2α-[6-(tetrazol-5-yl)-cis-2-hexen-1-yl]-3β-[3α-(tetrahydropyran-2-yloxy)-4,4-dimethyl-5-(2-furyl)-trans-1-penten-1-yl]cyclopentanone (25)

To a solution cooled to −15° under nitrogen, of 662 mg. (1.22 mmole) 5α-hydroxy-3α-(tetrahydropyran-2-yloxy)-2β-[3α-(tetrahydropyran-2-yloxy)-4,4-dimethyl-5-(2-furyl)-1-trans-1-penten-1-yl]-1α-[6-(tetrazol-5-yl)-cis-2-hexen-1-yl]cyclopentane (23) in 15 ml. reagent grade acetone was added dropwise 0.615 ml. of Jones' reagent. After 15 minutes at −10°, 0.615 ml. 2-propanol was added and the reaction mixture was allowed to stir an additional 5 minutes at which time it was combined with 75 ml. ethyl acetate, washed with water (3×10 ml.), dried (MgSO₄) and concentrated to give 477 mg. of the colorless, oily 4α-(tetrahydropyran-2-yloxy)-2α-[6-(tetrazol-5-yl)-cis-2-hexen-1-yl]-3β-(3α-tetrahydropyran-2-yloxy)-4,4-dimethyl-5-(2-furyl)-trans-1-penten-1-yl]cyclopentanone (25).

EXAMPLE 23

4α-hydroxy-2α-[6-(tetrazol-5-yl)-cis-2-hexen-1-yl]-3β-(3α-hydroxy-4,4-dimethyl-5-(2-furyl)-1-trans-1-penten-1-yl) cyclopentanone (26)

A solution of 489 mg. 4α-(tetrahydropyran-2-yloxy)-2α-[6-tetrazol-5-yl)-cis-2-hexen-1-yl]-3β-[3α-(tetrahydropyran-2-yloxy-4,4-dimethyl-5-(2-furyl)-trans-1-penten-1-yl]cyclopentanone (25) in 10 ml. of a 65:35 mixture of glacial acetic acid:water was stirred under nitrogen at 25° for 20 hours then was concentrated by rotary evaporation. The resultant crude oil was purified by column chromatography on silica gel (Mallinckrodt CC-7 100–200 mesh) using mixtures of chloroform:ethyl acetate as eluents. After elution of less polar impurities the oil 4α-hydroxy-2α-[6-(tetrazol-5-yl)-cis-2-hexen-1-yl]-3β-(3α-hydroxy-4,4-dimethyl-5-(2-furyl)-1-trans-1-penten-1-yl) cyclopentanone (26) weighing 157 mg. was collected.

EXAMPLE 24

N-methanesulfonyl 9α-hydroxy-11α,15α-bis-(tetrahydropyran-2-yloxy-5-cis-13-trans-16,16-dimethyl-17-(2-furyl)-ω-trisnorprostadienamide (27)

To a solution of 3.9 g. (7.5 mmole) [4-(methanesulfonylaminocarbonyl)-n-butyl]triphenylphosphonium bromide in a dry nitrogen atmosphere in 8.0 ml. dry dimethyl sulfoxide was added 7.75 ml. (14.5 mmole) of a 1.87 M solution of sodium methylsulfinylmethide in dimethyl sulfoxide. To this red ylide solution was added dropwise a solution of 1.22 g. (2.50 mmole) 2-[5α-hydroxy-3α-(tetrahydropyran-2-yloxy)-2β-(3α-[tetrahydropyran-2-yloxy]-4,4-dimethyl-5-(2-furyl)-trans-1-penten-1-yl)cyclopent-1α-yl]-acetaldehyde, γ-hemiacetal (22) in 5.0 ml. dry dimethyl sulfoxide over a period of 20 minutes. After an additional 18 hours stirring at room temperature, the reaction mixture was poured onto ice water. The basic aqueous solution was acidified to ca. pH 3 with 1 N aqueous hydrochloric acid. The acidic solution was extracted with ethyl acetate (3×20 ml.) and the combined organic extracts washed once with water (10 ml.), dried (MgSO₄) and evaporated to a solid residue. This solid residue was triturated with ether and filtered. The filtrate was purified by column chromatography on silica gel (Baker "Analyzed" Reagent 60–200 mesh) using 2% dimethyl amine in ethyl acetate then 10% methanol in methylene chloride as eluents. After removal of high $R_f$ impurities, the desired N-methanesulfonyl 9α-hydroxy-11α, 15α-bis-(tetrahydropyran-2-yloxy)-5-cis-13-trans-16,16-dimethyl-17-(2-furyl)-ω-trisnorprostadienamide (27) was collected as a colorless oil weighing 1.14 g.

EXAMPLE 25

N-methanesulfonyl 9α,11α,15α-trihydroxy-5-cis-13-trans-16,16-dimethyl-17-(2-furyl)-ω-trisnorprostadienamide (28)

A solution of 461 mg. (0.72 mmole) N-methanesulfonyl 9α-hydroxy-11α,15α-bis-(tetrahydropyran-2-yloxy)-5-cis-13-trans-16,16-dimethyl-17-(2-furyl)-ω-trisnorprostadienamide (27) in 10.0 ml. of a 65:35 mixture of glacial acetic acid:water was stirred under nitrogen at 25° for 18 hours then was concentrated by rotary evaporation. The resultant crude oil was purified by column chromatography on silica gel (Mallinckrodt CC-7 100–200 mesh) using mixtures of chloroform:ethyl acetate as eluent. After elution of less polar impurities the colorless, oily N-methanesulfonyl 9α,11α,15α-trihydroxy-5-cis-13-trans-16,16-dimethyl-17-(2-furyl)-ω-trisnorprostadienamide (28) weighing 151 mg. was collected.

EXAMPLE 26

N-methanesulfonyl 9-oxo-11α,15α-bis-(tetrahydropyran-2-yloxy)-5-cis-13-trans-16,16-dimethyl-17-(2-furyl)-ω-trisnorprostadienamide (29)

To a solution cooled to −15° under nitrogen, of 680 mg. (1.06 mmole) N-methanesulfonyl 9α-hydroxy-11α,15α-bis-(tetrahydropyran-2-yloxy)-5-cis-13-trans-16,16-dimethyl-17-(2-furyl)-ω-trisnorprostadienamide (27) in 15 ml. reagent grade acetone was added dropwise 0.54 ml. of Jones' reagent. After 15 minutes at −10°, 0.54 ml. 2-propanol was added and the reaction mixture was allowed to stir an additional 5 minutes at which time it was combined with 75 ml. ethyl acetate, washed with water (3×10 ml.), dried (MgSO$_4$) and concentrated to give 489 mg. of the colorless, oily N-methanesulfonyl 9-oxo-11α,15α-bis-(tetrahydropyran-2-yloxy)-5-cis-13-trans-16,16-dimethyl-17-(2-furyl)-ω-trisnorprostadienamide (29).

EXAMPLE 27

N-methanesulfonyl 9-oxo-11α,15α-dihydroxy-5-cis-13-trans-16,16-dimethyl-17-(2-furyl)-ω-trisnorprostadienamide (30)

A solution of 489 mg. N-methanesulfonyl 9-oxo-11α,15α-bis-(tetrahydropyran-2-yloxy)-5-cis-13-trans-16,16-dimethyl-17-(2-furyl)-ω-trisnorprostadienamide (29) in 10 ml. of a 65:35 mixture of glacial acetic acid:water was stirred under nitrogen at 25° for 20 hours then was concentrated by rotary evaporation. The resultant crude oil was purified by column chromatography on silica gel (Mallinckrodt CC-7 100–200 mesh) using mixtures of chloroform:ethyl acetate as eluents. After elution of less polar impurities the oily N-methanesulfonyl 9-oxo-11α,15α-dihydroxy-5-cis-13-trans-16,16-dimethyl-17-(2-furyl)-ω-trisnorprostadienamide (30) weighing 157 mg. was collected.

EXAMPLE 28

N-methanesulfonyl-9α-Hydroxy-11α,15α-bis-(tetrahydropyran-2-yloxy)-16,16-dimethyl-17-(2-furyl)-trans-13-ω-trisnorprostenamide (30)

A solution cooled to −20° of 1.0 mmole of N-methanesulfonyl-9α-hydroxy-11α,15α-bis-(tetrahydropyran-2-yloxy-5-cis-13-trans-16,16-dimethyl-17-(2-furyl)-ω-trisnorprostadienamide acid (27) in 50 ml. methanol is hydrogenated in an atmospheric hydrogenation apparatus using 1 g. of 10% palladium-on-carbon as a catalyst and a hydrogen atmosphere. After the hydrogenation is essentially complete, the catalyst can be filtered from the reaction mixture and the solvent can be removed in vacuo from the resultant filtrate. The residue can be purified by the common techniques such as column or liquid high pressure chromotography to yield the title compound.

In addition the other 11,15-bis(THP) PGF$_{1\alpha}$ intermediates of the present invention may be synthesized by the method of Example 28 by substituting the appropriate 11,15-bis(THP) PGF$_{2\alpha}$ intermediate from Example 6, 10, 14, 20 or 24 for compound (27) of Example 28.

EXAMPLE 29

N-methanesulfonyl-9α,11α,15α-trihydroxy-16,16-dimethyl-17-(2-furyl)-trans-13-ω-trisnorprostenamide (31)

A solution of 1.0 mmole of N-methanesulfonyl-9α-hydroxy-11α,15α-bis(tetrahydropyran-2-yloxy)-16,16-dimethyl-17-(2-furyl)-trans-13-ω-trisnorprostenamide (30) in 10.0 ml. of 65:35 mixture of glacial acetic acid-water is stirred under nitrogen at 25° for ca. 18 hrs. then is concentrated by rotary evaporation. The residue can then be purified by column chromatography on silica gel (100–200 SAE mesh) to yield the title compound.

In addition the other PGF$_{1\alpha}$ compounds of the present invention may be synthesized by the method of Example 29 by substituting the appropriate 11,15-bis(THP) PGF$_{1\alpha}$ intermediate from Example 28 for compound (30) of Example 29.

EXAMPLE 30

N-methanesulfonyl-9-oxo-11α,15α-bis-(tetrahydropyran-2-yloxy)-13-trans-16,16-dimethyl-17-(2-furyl)-ω-trisnorprostenamide (32)

To a solution cooled to −15° under nitrogen, of 1.0 mmole N-methanesulfonyl-9α-hydroxy-13-trans-11α,15α-bis-(tetrahydropyran-2-yloxy)-16,16-dimethyl-17-(2-furyl)-ω-trisnorprostenamide (30) in 15 ml. reagent grade acetone is added dropwise 0.54 ml. of Jones' reagent. After 15 minutes at −10°, 0.54 ml. 2-propanol is added and the reaction mixture is allowed to stir an additional 5 minutes, then purified by extraction to yield the title compound.

EXAMPLE 31

N-methanesulfonyl-9-oxo-11α,15α-dihydroxy-16,16-dimethyl-17-(2-furyl)-ω-trisnorprostenamide (33)

A solution of 1.0 mmole N-methanesulfonyl-9-oxo-11α,15α-bis-(tetrahydropyran-2-yloxy)-13-trans-16,16-dimethyl-17-(2-furyl)-ω-trisnorprostenamide (32) in 10 ml. of a 65:35 mixture of glacial acetic acid:water is stirred under nitrogen at 25° for ca. 20 hours then is concentrated by rotary evaporation. The residue can be purified by column chromatography on silica gel (100–200 SAE mesh) to yield the title compound.

In addition the other $PGE_1$ compounds of the present invention may be synthesized by the methods of Example 30 and 31 by substituting the appropriate 11,15-bis(THP) $PGF_{1\alpha}$ intermediate from Example 28 for compound (31) of Example 30.

What is claimed is:

1. 2-Descarboxy-2-(tetrazol-5-yl)-16,16-dimethyl-17-(2-furyl)-$\omega$-trisnorprostaglandin $E_2$.

* * * * *